United States Patent [19]  
Garfield et al.

[11] Patent Number: 5,397,344  
[45] Date of Patent: Mar. 14, 1995

[54] METHODS OF AND APPARATUS FOR MEASURING UTERINE ELECTRICAL AND MECHANICAL ACTIVITY

[75] Inventors: Robert Garfield, Friendswood, Tex.; Krzysztof Chwalisz; Radoslaw Bukowski, both of Berlin, Germany

[73] Assignee: Schering Aktiengesellschaft, Berlin and Bergkamen, Germany

[21] Appl. No.: 995,180

[22] Filed: Dec. 22, 1992

[51] Int. Cl.$^6$ .............................................. A61N 1/00
[52] U.S. Cl. .................................... 607/138; 128/642
[58] Field of Search ..................... 128/420.5, 639, 642, 128/733, 734, 783, 784, 786, 788; 607/39, 115, 116, 138

[56] References Cited

U.S. PATENT DOCUMENTS

| | | | |
|---|---|---|---|
| 2,924,213 | 2/1960 | Fleck | 128/642 |
| 3,313,293 | 4/1967 | Chesebrough et al. | 128/642 |
| 4,577,640 | 3/1986 | Hofmeister | 128/733 |
| 4,630,611 | 12/1986 | King | 128/786 |
| 4,848,352 | 7/1989 | Pohndorf et al. | 128/642 |
| 4,890,623 | 1/1990 | Cook et al. | 128/786 |
| 4,967,761 | 11/1990 | Nathanielsz | 128/733 |
| 5,184,619 | 2/1993 | Austin | 128/639 |

OTHER PUBLICATIONS

Miller et al., *American Physiological Society*, pp. C130–C141 (1989).
Demianczuk et al., "Myometral electrophysiologic activity . . . ", Am. J. Obstet. Cynecol, Jul. 1, 1984, pp. 485–491.
McNellis et al., "Structural and Functional Studies of the Control . . . " The Onset of Labor: Cellular & Integrative Mechanisms, 1988, Perin. Press.
Miller et al., "Improved propagation in myometrium . . . ", Am. Journ. of Physiology, vol. 25, No. 1, Jan. 1989, pp. C130–C141.
Garfield et al., *Science*, vol. 198, pp. 958–960 (Dec. 2, 1977).
Garfield et al., *In Vitro Toxicology*, vol. 3, No. 1, pp. 41–59 (1990).
Chwalisz et al., *Am. J. Obstet. Gynecol.*, vol. 165, No. 6, Part I, pp. 1760–1770 (Dec. 1991).
Garfield, *The Onset of Labor: Cellular & Integrative Mechanisms*, pp. 55–79 (1988).
Garfield et al., *Am. J. Obstet. Gynecol.*, vol. 157, No. 5, pp. 1281–1285 (Nov. 1987).
Demianczuk et al., *Am. J. Obstet. Gynecol.*, vol. 149, No. 5, pp. 484–491 pp. 485–491 (Jul. 1, 1984).
Garfield, *Clinical Obstetrics and Gynecology*, vol. 27, No. 3, pp. 572–591 (Sep. 1984).
Puri et al., *Biology of Reproduction* 27, 967–957 (1982).
Garfield et al., *Am. J. Obstet. Gynecol.*, vol. 142, No. 1, pp. 21–27 (Jan. 1, 1982).
Garfield et al., *Am. J. Obstet. Gynecol.*, vol. 140, No. 3, pp. 254–260 (Jun. 1, 1981).
Garfield et al., *Can. J. Physiol. Pharmacol.*, vol. 70, pp. 481–490 (1992).
Morizaki et al., *Am. J. Obstet. Gynecol.*, vol. 160, No. 1, pp. 218–228 (Jan. 1989).
Bulat et al., *Can. J. Physiol. Pharmacol.*, vol. 67, pp. 837–844 (1989).
Buchanan et al., *The Anatomical Record* 221:611–618 (1988).

*Primary Examiner*—Max Hindenburg
*Attorney, Agent, or Firm*—Millen, White, Zelano & Branigan

[57] ABSTRACT

The existence of gap junctions between cells is detected by stimulating the cells with electrical pulses having selective parameters and then detecting propagated signals emitted by the cells. A needle is provided having stimulation electrodes thereon from which the stimulating pulses emanate and an array of recording electrodes for detecting the pulses. In an alternative embodiment, an array of piezoelectric electrodes is distributed within the array of recording electrodes. The signals detected by the recording electrodes and piezoelectric electrodes are monitored by a recording device and stored within a computer.

15 Claims, 6 Drawing Sheets

METHODS OF AND APPARATUS FOR MEASURING UTERINE ELECTRICAL AND MECHANICAL ACTIVITY

BACKGROUND OF THE INVENTION

The invention relates to methods of and apparatus for measuring uterine electrical and mechanical activity. More particularly, the invention relates to a method and instrument useful for determining the contractile state of the uterus by recording spontaneous and evoked electrical activity of the muscle cells of the uterus.

Preterm labor is one of the major pathological states most frequently complicating pregnancy. Preterm birth is the major cause of prenatal morbidity and mortality (75%) and long term neurological handicaps. In spite of the use of different new tocolytics, the incidence of preterm labor and the incidence of prenatal morbidity and mortality has not changed over the last decades.

The diagnosis of labor (term and preterm) is the most significant problem faced by obstetricians. Preterm labor is the pathological state most frequently associated with this dilemma. Moreover, term labor often requires adjuvant therapy to halt or augment labor. However, there is no currently available method to objectively diagnose when the uterus is prepared to labor either preterm or term. Since there is spontaneous uterine activity during pregnancy, it is often not possible to distinguish between physiological uterine activity or preterm labor. The state of the cervix is commonly used as a predictor of preterm birth. However, the softening of the cervix, as well as the appearance of uterine contractions are relatively late in preterm labor.

Antiprogestins induce preparatory changes in the uterus in all stages of pregnancy. This results in the increase in myometrial responsiveness to oxytocic stimuli such as oxytocin or prostaglandins. The major effect of antiprogestins on the uterus is the preparation or conditioning of the myometrium to labor and delivery by inducing intercellular coupling which manifests itself by an increase in propagation due to an increase in gap junctions.

The uterus is quiescent throughout pregnancy to maintain a tranquil environment for the growing fetus. At the end of pregnancy normally the uterus begins to contract forcefully in a phasic manner (labor) to expel the fetus and other products of conceptions. Abnormally the uterus sometimes either begins to contract and labor prior to term (preterm labor) or fails to contract at term. Preterm labor occurs in about 10% of all pregnancies whereas the incidence of insufficient or absence of contractions at term is also very high (3 to 13%). In most cases the clinician is faced with the decision to either inhibit labor or stimulate it depending on the circumstances. However, the clinician has only subjective methods (state of cervix or number of contractions but not force of contraction) on which to base a decision.

The uterus is now known to pass through a series of steps prior to and during labor to prepare the muscle to contract in a coordinated, synchronous and therefore forceful manner. These steps include the development of gap junctions (low electrical resistance contacts), receptors and other events between and on the muscle cells that allow the uterus to contract as a syncytium and react to contractile agents. Contractions of the uterus are dependent upon electrical activity, therefore the presence of gap junctions is an important component of this process. These steps are known to be regulated by various physiological signals (hormones) and can be controlled pharmacologically. When the muscle cells pass through this state they become electrically and metabolically coupled. This state allows the uterus to contract forcefully and frequently. Although this process is known to occur during pregnancy, it also appears during the menstrual cycle and may be present in various pathological conditions of the uterus such as dysmenorrhea, endometriosis, habitual abortion, allergic reactions, etc. However, at present, the obstetrician or gynecologist has no objective method to evaluate this process. The clinical judgement as to treatment would be greatly enhanced by procedures which could define the state of the patient's uterus.

Numerous studies show that gap junctions are present in almost all cells and their presence and function has been associated with normal physiological control. Gap junctions are also known to be altered either structurally or functionally in pathological states such as cancer, hypoxia, inflammation, etc. Many studies demonstrate that one can assess gap junction presence or function by electrical simulation and recording of electrical events in adjacent cells.

There have been a number of studies with respect to this matter such as Miller, S. M., et al., "Improved Propagation in Myometrium Associated with Gap Junctions During Parturition", *American Journal of Physiology*, pages 130–141 (1989), incorporated herein by reference, in which gap junction measurements were made on uterine tissue of pregnant rats. Additional studies which are reported in the literature include: Garfield et al., "Gap Junctions: Their Presence and Necessity in Myometrium During Parturition", *Science*, Vol. 198, pp. 958–960 (Dec. 2, 1977); Miller et al., "Improved Propagation in Myometrium Associated with Gap Junctions During Parturition", American Physiological Society, pp. C130–C141 (1989); Garfield et al., "Modulation of Myometrial Gap Junctions: Toxicological Implications", *In Vitro Toxicology, A Journal of Molecular and Cellular Toxicology*, Vol. 3, Number 1, pp. 41–59 (1990); Chwalisz et al., "The Progesterone Antagonist Onapristone Increases the Effectiveness of Oxytocin to Produce Delivery without Changing the Myometrial Oxytocin Receptor Concentrations", *Am. J. Obstet. Gynecol.*, Vol. 165, No. 6, Part I, pp. 1760–1770 (December 1991); Garfield, "Structural and Functional Studies of the Control of Myometrial Contractility and Labor", *The Onset of Labor: Cellular & Integrative Mechanisms*, pp. 55–79 (1988); Garfield et al., "Effects of the Antiprogesterone RU 486 on Preterm Birth in the Rat", *American Journal of Obstetrics and Gynecology*, Vol. 157, No. 5, pp. 1281–1285 (November 1987); Demianczuk et al., "Myometrial Electrophysiologic Activity and Gap Junctions in the Pregnant Rabbit", *American Journal of Obstetrics and Gynecology*, Vol. 149, No. 5, pp. 485–491 (Jul. 1, 1984); Garfield, "Control of Myometrial Function in Preterm Versus Term Labor", *Clinical Obstetrics and Gynecology*, Vol. 27, No. 3, pp. 572–591 (September 1984); Puri et al., "Changes in Hormone Levels and Gap Junctions in the Rat Uterus During Pregnancy and Parturition", *Biology of Reproduction*, 27, 967–975 (1982); Garfield et al., "Endocrine, Structural, and Functional Changes in the Uterus During Premature Labor", *American Journal of Obstetrics and Gynecology*, Vol. 142, No. 1, pp. 21–27 (Jan. 1, 1982); Garfield et al., "Appearance of Gap Junctions in the Myometrium of Women During Labor", *American Journal of Obstetrics and Gynecology*, Vol. 140, No. 3, pp. 254–260 (Jun. 1, 1981); Garfield et al., "Presence of Gap Junctions in the Myometrium of Women During Various Stages of Menstruation", *American Journal of Obstetrics and Gynecology*, Vol. 138, No. 5, pp. 569–574 (Nov. 1, 1980); and Garfield et al., "Are Gap Junctions Necessary for Cell-to-Cell Coupling of Smooth Muscle?: An Update", *Can. J. Physiol. Pharmacol.*, Vol. 70, pp. 481–490 (1992); each of which is incorporated herein by reference. While these studies each recognize various aspects of the phenomenon of interest, they do not suggest just how one would utilize the phenomenon in practical medical procedure.

The status (function, location, identification, etc.) of nerves and their terminals in tissues can be quantified also by selectively stimulating the nerves with electrical parameters that do not affect surrounding tissues. This so-called "field stimulation" has been used in many studies to activate nerves or their varicosities in tissues to assess, localize and identify nerves in tissues. Exemplary of such studies are the following articles: Garfield et al., "A Functional and Structural Study of the Innervation of the Human Uterus", *American Journal of Obstetrics and Gynecology*, Vol. 160, No. 1, pp. 218–228, (January 1989); Bulat et al., "Studies of the Innervation of Rabbit Myometrium and Cervix", *Can. J. Physiol. Pharmacol.*, Vol. 67, pp. 837–844 (1989); and Buchanan et al., "Innervation and Gap Junction Formation in the Myometrium of Pregnant Little Brown Bats, *Myotis lucifugus*", *The Anatomical Record* 221:611–618 (1988), each of which is incorporated herein by reference.

Prior methods and instruments for evaluating the status of the uterus have used external monitors which give little information of quantitative nature necessary to define the processes described above.

SUMMARY OF THE INVENTION

An object of the present method and invention is to measure in vivo the electrical and mechanical activity of tissues, such as for example, but not limited to, uterine muscle tissue, to produce a more quantitative, comprehensive and analytical framework of the tissue by transferring information from the tissue to a monitor for assessment by an attending physician or other party interested in monitoring the tissue.

Upon further study of the specification and appended claims, further objects and advantages of this invention will become apparent to those skilled in the art.

The present method and apparatus is applicable to a wide range of obstetrical, gynecological and other conditions. One such application is defining the state of the uterus during term and preterm labor. Another application is monitoring the nonpregnant uterus for indication of conditions such as infertility and uterine pathology in cycling women. The method and apparatus is also valuable for use in connection with other tissues other than the uterus such as tissues of the bladder, intestine, heart and other muscular or nonmuscular (brain, liver, pancreas, etc.) tissues for purposes of evaluating their normal and abnormal behavior. The method and instrument is also usable for monitoring tissues in animals, as for example in a veterinary clinic or for live stock.

In accordance with one specific aspect of the invention, a needle includes stimulating recording electrodes as well as optional miniature piezoelectric electrodes embedded along an inner surface thereof. In accordance with one embodiment, the needle is placed in the uterine wall (i.e., myometrium) under ultrasound guidance similar to routine procedures during amniotic fluid sampling. The signals detected by the needle are monitored to provide measurements indicative of spontaneous and electrically evoked activity. The needle is connected to a multichannel recorder, stimulator and computer with software for analysis of signals.

The above-described needle may alternatively be hollow for withdrawing material, such as for example amniotic fluid.

Alternative embodiments of the needle utilize electrodes mounted on the exterior thereof.

Further embodiments of the method include mounting only the stimulation electrodes on the needle for eliciting electrical activity of tissue and placing recording electrodes on the surface of a patient's skin to measure conducted activity. A further embodiment of the method contemplates placing a simulating and recording electrode separately at two or more locations in the uterine wall. A further embodiment involves modification of the current pulses from the stimulator to selectively stimulate only nerve cells and record nerve transmitter responses in muscle or other cells.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION

Figure 1:
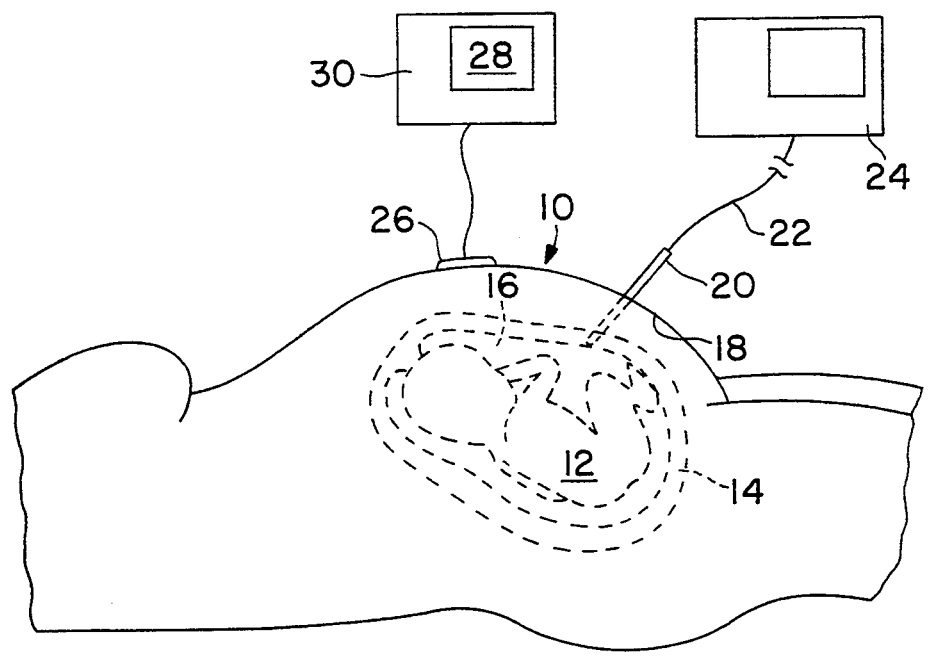
FIG. 1 is a side view, partially in phantom, showing a needle configured in accordance with the instant invention inserted in the uterine wall of a pregnant patient, the needle being connected to a recording device and the position of the needle being monitored by an ultrasonic scanner.

Referring now to FIG. 1, there is shown schematically a pregnant patient 10 with a fetus 12 retained with a uterine wall 14 which defines an amniotic cavity 16 having amniotic fluid therein. The uterine wall 14 is primarily configured of muscle tissue and is disposed proximate the abdominal wall 18 of the patient 10. In accordance with the principles of the instant invention, a needle 20 is passed from the exterior of the patient 10 through the abdominal wall 18 and embedded in the uterine wall 14. The needle has a bundle of leads 22 which are connected to a recording apparatus 24.

In accordance with the principles of the instant invention, the uterus of the pregnant patient 10 is monitored by ultrasonic transducers 26 to provide an image 28 of the uterine wall on an ultrasonic monitor 30 so that the shank 31 of the needle 20 may be accurately guided and properly embedded in the uterine wall 14.

Figure 2:
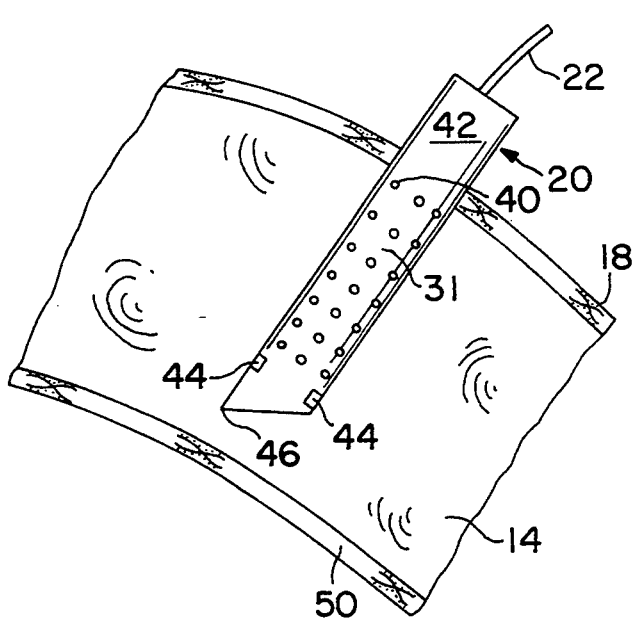
FIG. 2 is an enlarged, side elevational view illustrating the needle of FIG. 1 embedded in the muscle tissue of the uterine wall.

Referring now to FIG. 2, a greatly enlarged view of a section of uterine wall 14 is shown with the shank 31 of the needle 20 embedded therein after having been passed through the abdominal wall 18. The needle 20 is preferably made of stainless steel and has an overall length of about 65 mm. An array of recording electrodes 40 are disposed on the cylindrical surface 42 of the needle 20 and an array of stimulation electrodes 44 are positioned proximate the tip 46 of the needle. The arrays of recording and stimulation electrodes 40 and 44 are completely embedded in the muscle tissue of the uterine wall 14 with the muscle tissue extending into the hollow core of the needle. In accordance with one embodiment of the invention, the tip 46 of the needle to isolate a portion of the muscle tissue within the hollow core of the needle 20 does not penetrate the endometrium 50 which is disposed between the muscle 14 of the uterine wall and the amniotic fluid 16. In accordance with another embodiment of the invention, the needle 20 is a hollow amniotic fluid sampling needle which performs fluid sampling alternative to electrical monitoring.

Figure 3:
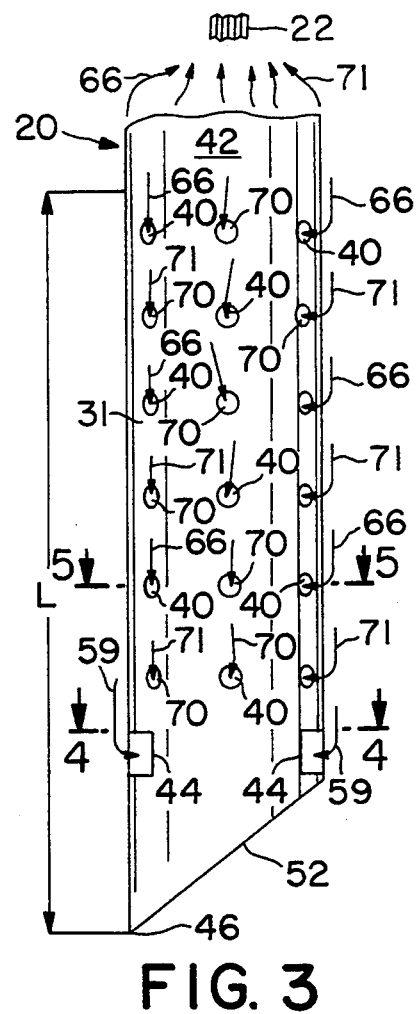
FIG. 3 is a further enlarged side view showing a portion of the exterior surface of the needle shown in FIGS. 1 and 2.

Referring now to FIG. 3, there is shown a side view of the needle 20 where it is seen that the embedded portion of the needle having the array of recording electrodes 40 and stimulating electrodes 44 has a length L of about 2–4 mm and a diameter of about 0.5 to 2 mm. The recording electrodes 40 are spaced from one another by a distance of about 0.5 mm, while the stimulation electrodes 44 are a height and width of about 0.5 mm. The tip 46 of the needle 20 is disposed approximately 0.5 mm from the bottom of the array of stimulation electrodes 44 and has a sloping edge 52 extending from one side of the needle to the tip 46 thereof. The dimensions defining spaces between various electrodes are suggested dimensions which may be varied from needle to needle to optimize performance of the needles 20.

Figure 4:
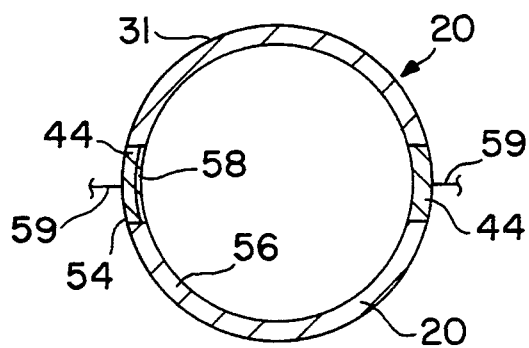
FIG. 4 is a sectional view taken along lines 4—4 of FIG. 3 showing an array of stimulation electrodes.

Referring now to FIG. 4, where the shank 31 of the needle 20 is shown in cross-section, the stimulation electrodes 44 are silver plated into indentations 54 of the wall 56 of the needle. The indentations 54 are first coated with an insulating material 58 to electrically isolate the stimulation electrodes 44 from the stainless steel needle shank 31. Each stimulation electrode 44 has an insulated lead 59 which is led back over the surface 42 of the needle 20 (see FIG. 3) into the lead bundle 22 and to the recording device 24 (see FIG. 1). The stimulation electrodes 44 receive either depolarized or hyperpolarized current pulses from the recording device 24, with each pulse having a duration in the range of about 10 to 500 milliseconds, a frequency in the range of 0.05 to 5 hertz and an amplitude in the range of about 0.1 to 30 volts.

Figure 5:
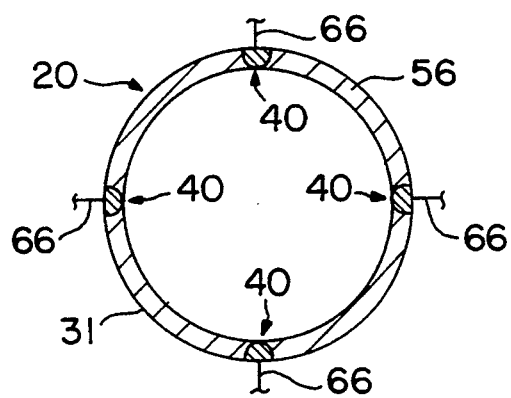
FIG. 5 is a cross-section taken along lines 5—5 of FIG. 3 showing an array of recording electrodes.
Figure 6:
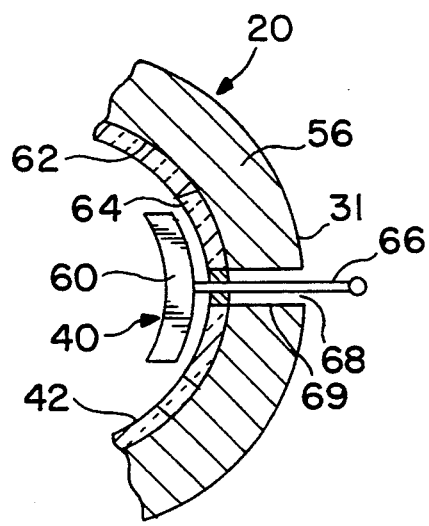
FIG. 6 is an enlarged sectional view of a portion of FIG. 5 showing how an individual recording electrode is mounted within the needle.

Referring now to FIGS. 5 and 6 there is shown the specific structure of one level of the array of recording electrodes 40 as well as the structure of a single recording electrode. In the illustrated embodiment, there are four recording electrodes disposed at 90° intervals around the wall 56 of the needle 20. As is seen in the specific embodiment of FIG. 6, each recording electrode 40 includes a plate 60 made of silver or another conductive material which is disposed inside of the needle 20 proximate the inner surface 62 of the wall 56. A layer of electrical insulation 64 is disposed between the plate 60 and the surface 62 of the wall 56 to electrically isolate the plate 60 from the stainless steel needle shank 31. An insulated lead 66 extends through a bore 68 through the wall of the needle 56 and a hole 69 in the insulation. As is seen in FIG. 1, the lead 66 from each recording electrode 40 extends back up in the needle and into the lead bundle 22 for connection to the recording apparatus 24. The sliver plate 60 functions similar to an antenna and receiver signals generated in the muscle tissue 14 (see FIG. 2).

In an alternative apparatus, instead of all the electrodes 40 being recording electrodes, the electrodes may be piezoelectric electrodes 70 which sense contractual events and transmit these events via insulated leads 71 to the recording apparatus 24. Preferably, the piezoelectric electrodes 70 are disposed between the recording electrodes to provide an alternating array as is shown in FIG. 3.

Figure 7:
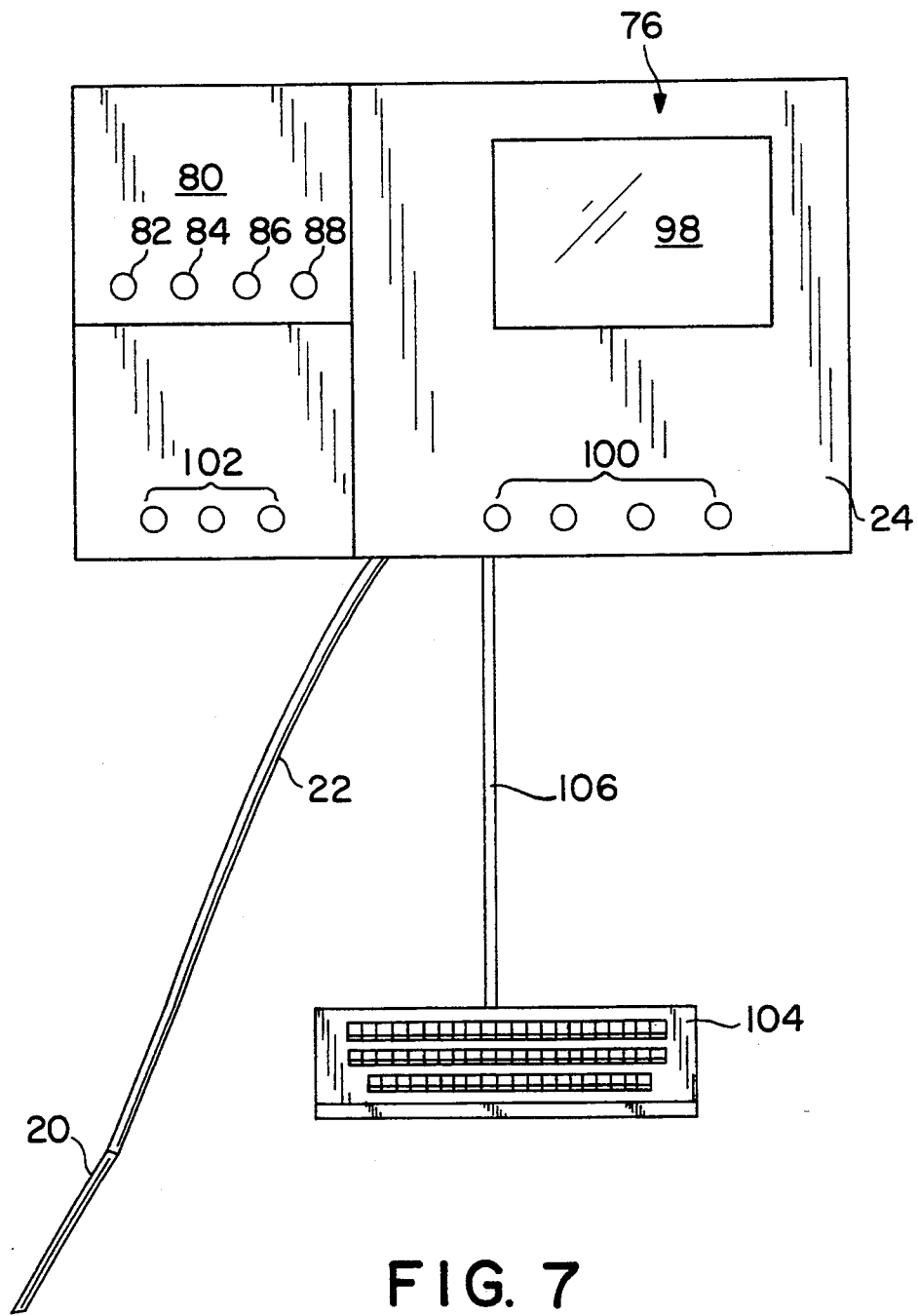
FIG. 7 is a front view of a typical recording apparatus to which the needle is connected and which provides stimulation signals and receives response signals.

Referring now to FIG. 7, where the recording apparatus 24 is shown, the recording apparatus includes a stimulator 80 for invoking electrical events in the needle 20. The stimulator 80 is of conventional design and includes a control for amplitude 82, a control for voltage 84, a control for duration 86 and a control for frequency 88. The stimulator is connected via cable bundle 22 to the stimulation electrodes 44 via leads 59. The recording apparatus 24 also includes a monitor 96 with a monitor screen 98 to display readings from the electrical leads 66 and 71 connected to the recording electrodes 40 and piezoelectric electrodes 70, respectively. In a conventional fashion, the monitor includes controls 100 for selecting various arrays of electrodes to be detected. For example, the controls may select the recording electrodes 40 or the piezoelectric electrodes 70 for monitoring. Finally, recording apparatus 24 also includes controls 102 for amplifying and filtering the signals relayed over leads 41 and 71 to the monitor 96. A standard computer 104 is connected to the monitor 24 via cable 106. The computer 104 includes software and a key board for controlling the various functions of the recording apparatus 24.

Figure 8:
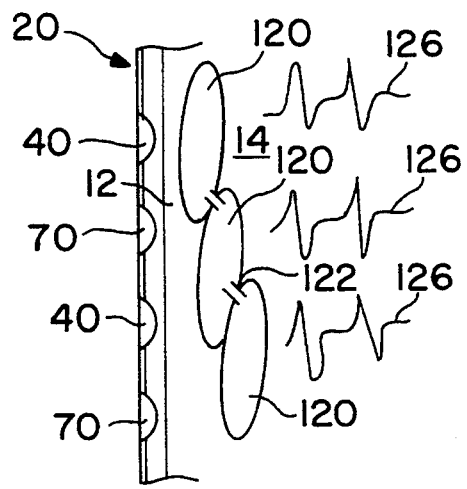
FIG. 8 is a schematic view of smooth muscle tissue in proximity with the needle of FIGS. 1–7 illustrating the function of the instant invention.

Referring now to FIG. 8, it is seen that the needle 20 with the arrays of recording electrodes 40 and piezoelectric electrodes 70 are disposed proximate muscle cells 120 in the smooth muscle tissue of the uterine wall 14. Between each cell 120 and adjacent cells 120, there is schematically illustrated what is known a gap junction 122 which is a low resistance electrical contact that develops prior to and during labor in order to prepare the smooth muscle tissue 14 for contraction in a coordinated and synchronous manner. Contractions of the uterine wall 14 are dependent upon propagation of electrical activity between the muscle cells; therefore, the presence of the gap junctions 122 is an important component of the contraction process. Gap junctions are known to be regulated by various physiological signals produced by hormones and can be controlled pharmacologically. When the muscle cells 120 contain open gap junctions, they become electrically and metabolically coupled which allows the uterus wall 44 to contract forcefully and frequently.

In accordance with the instant invention, the smooth muscle tissue 14 is stimulated with electrical pulses having parameters that affect only the cells 120 and not surrounding tissue. Monitoring is initiated by pulsing the stimulation electrodes 44 (FIGS. 2-4) with current pulses having a duration in the range of about 10 to 500 milliseconds at a frequency in the range of about 0.05 to 5 hertz and at a voltage amplitude in the range of about 0.1 to 30 volts. This stimulation causes spontaneous and electrically evoked action potentials 126 at the recording electrodes 40 as well mechanical interactions with the piezoelectric electrodes 70, which signals are transmitted over the leads 66 from the recording electrodes and leads 71 from the piezoelectric electrodes to the recording apparatus 24. In the recording apparatus 24 the amplifier 101 modulates the signals using a time constant of about 1 second at a high frequency filtration band pass in the range of 0.1 to 22 hertz. The thus monitored signals 126 are displayed on the monitor screen 98, then stored PC computer-based hardware and software in the computer 104 with a sampling rate of about 500 digitized samples per second.

Figure 9:
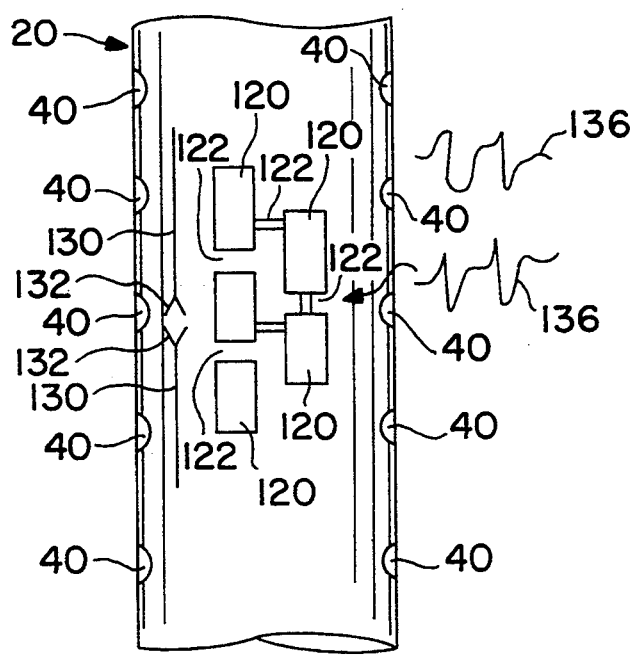
FIG. 9 is a view similar to FIG. 8 showing smooth muscle or other tissue with nerves proximate the needle of the instant invention and further illustrating an additional feature of the invention.

Referring now to FIG. 9, there is schematically shown the needle 12 and recording electrodes 40 in juxtaposition with cells 120 being in a state where there are gap junctions 122. Muscle tissue, which may be smooth muscle tissue or other muscle tissue, has peripheral nerves 130 therein with nerve endings 132. It is possible to stimulate nerves 130 and nerve endings 132 by pulsing the stimulation electrodes 44 (FIGS. 2, 3, 4) with parameters that do not activate the cells 120. The nerves 130 then act on the cells 120 and the cells generate signals 136 in the cells 120 which are detected by the electrodes 40. In this way, a physician is able to monitor the effects of nerve stimulation in isolation on the cells 120.

Referring now to FIGS. 10-15, the recording apparatus 24 stores signals 126 in the associated computer 104 and extracts the following parameters derived from the signals 126:

a. duration of bursts of action potentials 126;
b. propagation velocity of individual action potentials in bursts following stimulation (measured from change in latency from successive electrodes 40);
c. patterns of propagation and distance of propagation during spontaneous and evoked action potentials;
d. entrainment of bursts;
e. velocity and distance of mechanical activity as measured by the piezoelectric electrodes 70;
f. characteristics of the contractions such as rate of rise and amplitude as detected by the piezoelectric electrodes; and
g. characteristics of the action potentials such as the rate of rise of depolarization and plateau, amplitude and the rate of repolarization.

Figure 10:
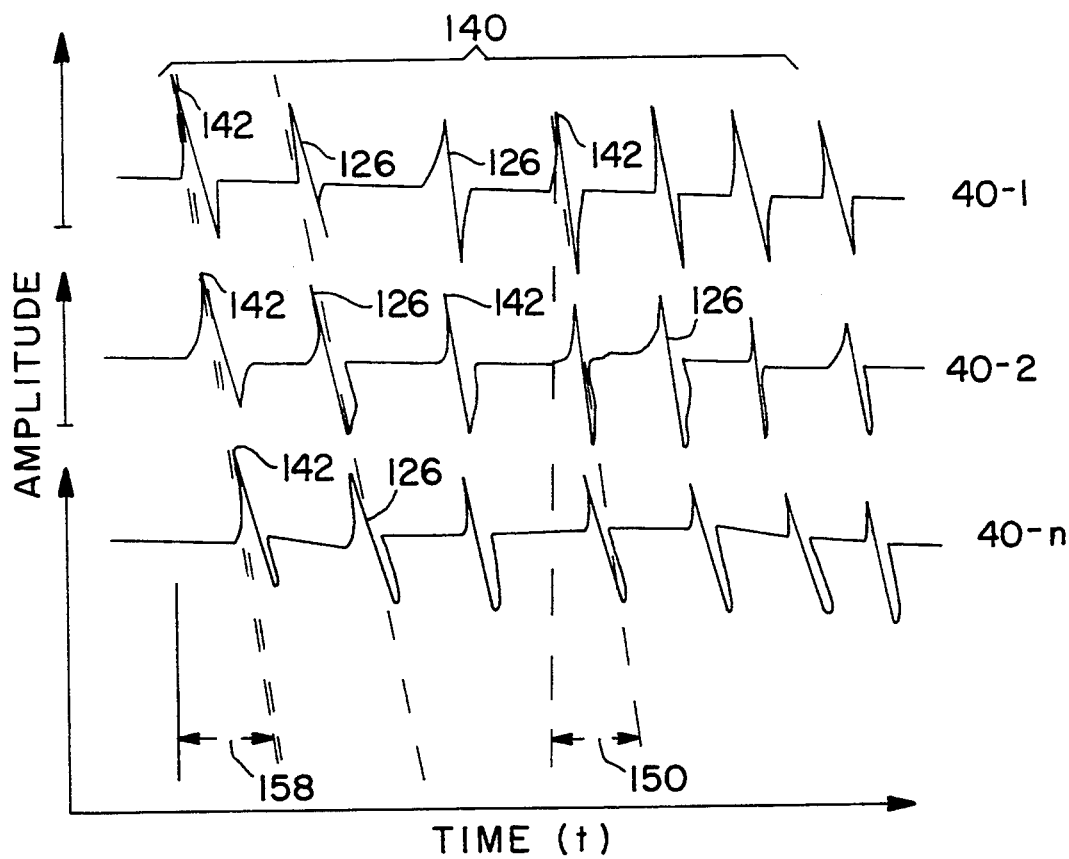
FIG. 10 is a diagrammatical view showing spontaneous electrical activity between cells detected by recording electrodes.

Considering the aforementioned parameters in more detail, as is seen in FIG. 10, the length of each burst 140 is plotted as a function of time t to provide the duration of each burst in seconds as detected by the electrodes 40-1 through 40-n. In addition, the computer 104 measures the action potential frequency in cycles per second by counting the number of spikes 142 per unit time.

Figure 11:
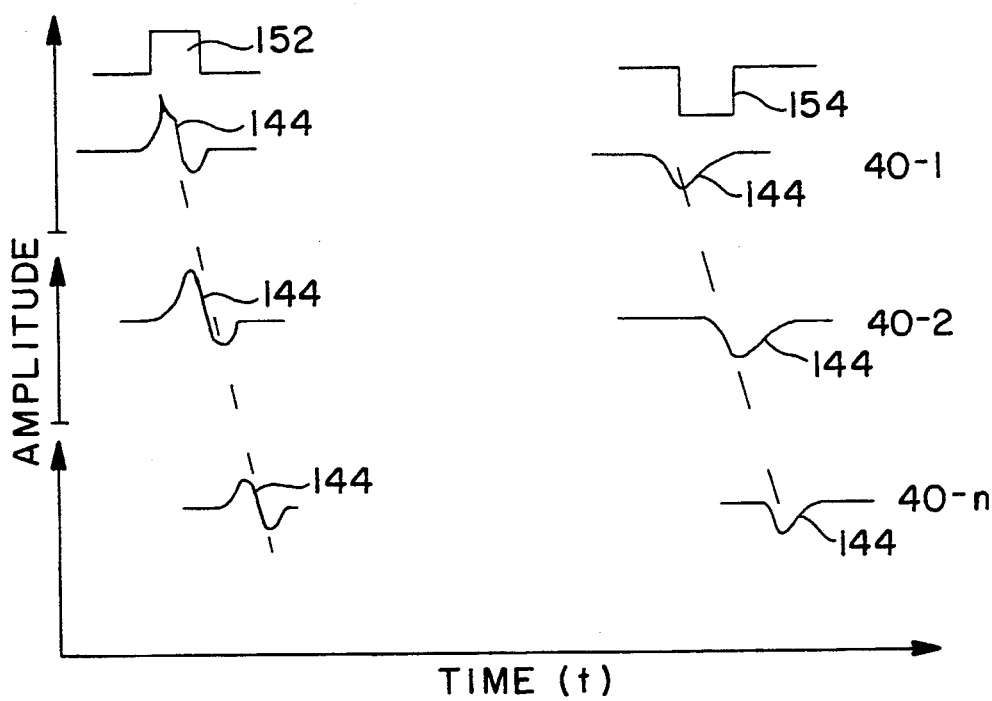
FIG. 11 is a diagrammatical view showing evoked electrical activity between cells.

The propagation obligation velocity of the individual action potentials 126 and evoked potentials 144 is seen from a consideration of FIGS. 10 and 11, wherein a latency period 150 between selective recording electrodes 40 is shown. In FIG. 11, the evoked electrical responses 126 from the electrodes 40 result from the application of a polarized pulse 152 or a hyperpolarized pulse 154 applied to the stimulation electrodes 44 (FIGS. 2, 3 and 4).

Figure 12:
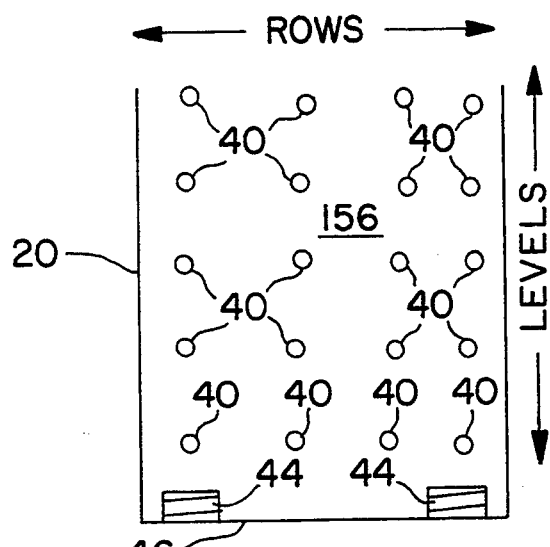
FIG. 12 is a linear diagram of an inner surface of the needle according to the instant invention with the recording electrodes arranged in a selected array.

Referring now to FIG. 12 in combination with FIGS. 10 and 11, a computer diagram of an array 156 of the electrodes 40 is shown with the electrodes arranged in levels and rows above the stimulation electrodes 44. The computer 104 computes the original and propagation characteristics of any of the bursts 140 shown in FIG. 10. Similarly, from stimulated potentials computer 104 calculates the propagation velocity in distance and displays this information on the screen 98 of the recording device 24. The entrainment of bursts 140 is seen by reference numeral 158 of FIG. 10 and is calculated from the initial latency period 160 between the bursts at each electrode 40.

Figure 13:
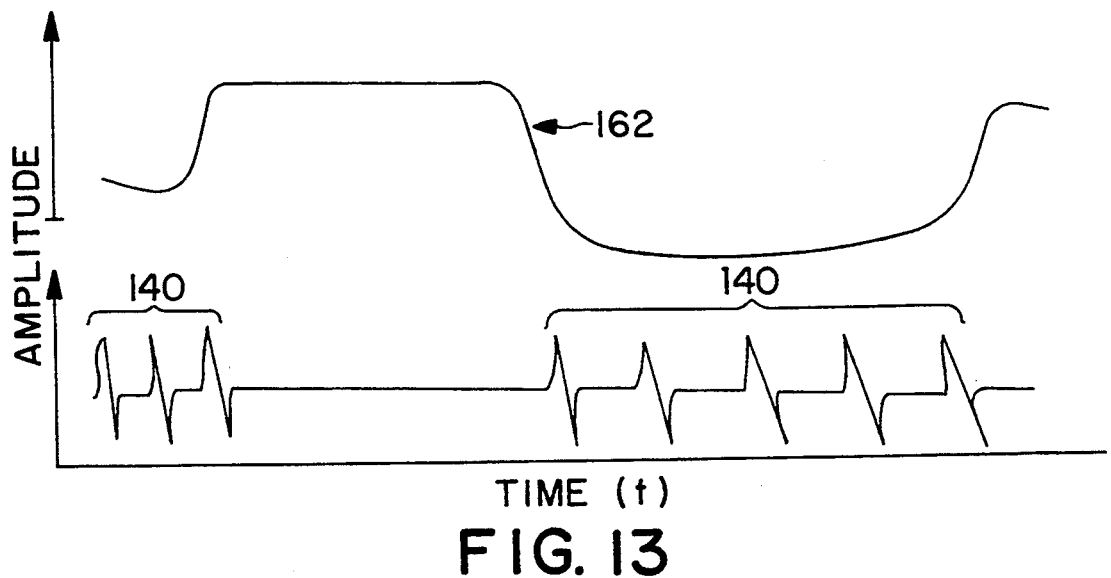
FIG. 13 is a diagrammatical view comprising cellular electrical activity in a muscle with muscle contractions.

Utilizing an approach similar to the approach for monitoring electrical activity, the computer 104 estimates the velocity and distance of the mechanical activity detected by the piezoelectrodes 70 (FIG. 3) which are indicative of the contractions of the uterine wall 14. As is seen in FIG. 13, the mechanical activity of muscle tissue comprising the uterus wall 14 is identified by a curve 162 which corresponds to the burst 140 indicative of the underlying electrical activity. Frequency, duration and magnitude of a contraction of the uterine wall 14 are respectively proportional to the frequency of the bursts 140, the duration of the bursts and the propagation of the action potential 126 to recruit additional cells 120 (see FIG. 8). The velocity of a contraction is estimated from the latency of contractions at successive piezoelectrodes 70 with the origin and distance of each contractual sequence being computed from a computer generated map of the needle 20 such as the map of FIG. 12 utilized for detecting action potentials 126.

Figure 14:
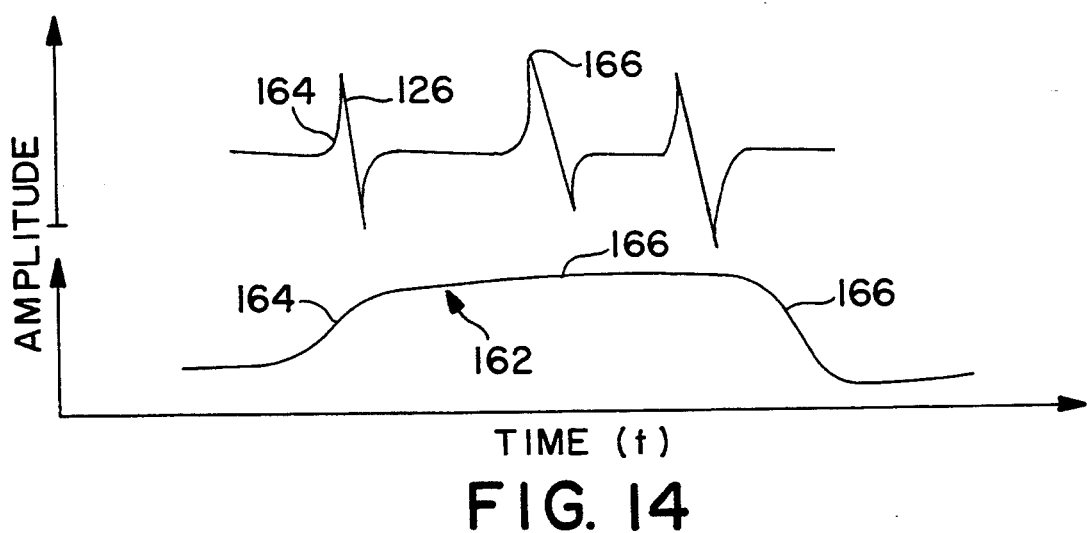
FIG. 14 is a diagrammatical view comparing cellular electrical activity and muscle contractions relating the rate of rise amplitude and the rates of depolarization and relaxation.

Referring now to FIG. 14, the characteristics of any contraction curve 162 or action potentials 126 contained in a burst 140 are isolated by the program of the computer 104. The rate of rise 164, amplitude 166, rate of repolarization and relaxation 166 can therefore be estimated.

From the aforedescribed measurements set forth in FIGS. 10-14, one can reasonably estimate if tissue, such as the muscle tissue of the uterine wall 14, or other tissue is coupled electrically. In other words, one can discern if the gap junctions 122 are present, absent or in a closed configuration. The presence of gap junctions 120 is generally indicative of the labor state for the uterine muscle comprising the uterine wall 14. On the other hand, the absence of electrical coupling suggests the ambience or closed state of the junctions and the lack of conditions favorable to labor.

While a preferred embodiment of the invention utilizes a signal needle 20 with both the stimulation electrodes 44 and the recording electrodes 40 thereon, in another embodiment of the invention, the stimulation electrodes 44 and recording electrodes 40 are on separate needles implanted at different locations. In another embodiment, the electrodes are mounted on the outside of the needle. In still another embodiment of the invention the stimulation electrodes 44 are embedded in the tissue being monitored while the recording electrodes 40 are positioned outside that tissue on the patient's skin.

While utilization of the apparatus and method has been described above as especially useful for monitoring the uterine wall 14 during pregnancy, gap junctions 122 are present in almost all cells and the presence and function thereof is associated with normal physiological control. Gap junctions 122 are also known to be altered either structurally or functionally in pathological states such as cancer, hypoxia, inflammation and other pathological states. Accordingly, it is within the scope of this invention to utilize the apparatus and methods thereof for medical and biological procedures other than uterine wall monitoring.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a combination with a recording device for monitoring and recording electrical signals, a needle useful for insertion into tissue having cells with gap junctions occurring therebetween, which cells generate electrical signals that propagate by gap junctions upon stimulation of the cells, the needle comprising:
  a hollow shank having an axis and a central cavity within which tissue is received;
  an array of recording electrodes disposed within the hollow shank for contact with the tissue therein, each of the recording electrodes having a first lead extending therefrom back to the recording device;
  an array of stimulation electrodes disposed in the hollow shank in spaced relation with respect to the recording electrodes for contact with the tissue therein, each stimulation electrode having a lead extending therefrom back to the recording device;
  the recording device including means connected to the second leads for applying stimulation signals over the second leads to the stimulation electrodes wherein the cells generate signals for detection by the recording electrodes and wherein the recording device includes means connected to the first leads extending from the recording electrodes for processing the signals.

2. The combination of claim 1, further including an array of piezoelectric electrodes disposed in the shank of the needle for detecting muscle contractions.

3. The combination of claim 1, wherein the stimulation electrodes and recording electrodes are axially spaced from one another with respect to the axis of the shank.

4. The combination of claim 3, further including an array of piezoelectric electrodes disposed in alternating fashion within the array of recording electrodes.

5. The combination of claim 4, wherein the stimulation electrodes are positioned proximate the tip of the needle with the recording and piezoelectric electrodes disposed between the stimulation electrodes proximate the end of the shank.

6. The combination of claim 5, wherein since the needle is hollow, whereby the needle may be used to withdraw fluid from a patient while alternatively monitoring the state of the cells with the electrodes.

7. An arrangement for detecting electrical coupling of cells in tissue by monitoring gap junctions between the cells, the arrangement comprising: a needle for insertion into the tissue, the needle having a hollow shank portion with a point for penetrating the tissue and isolating a portion of the cells from the remaining cells;
  at least one recording electrode within the hollow shank portion with a first lead extending from the recording electrode;
  at least one stimulation electrode within the hollow shank portion with a second lead extending from the stimulating electrode;
  a recording device including means connected to the second lead for applying stimulation signals to the stimulation electrode wherein the cells generate gap junction signals for detection by the recording electrode and the recording device further including means connected to the first lead for processing the gap junction signals.

8. The arrangement of claim 7, wherein the tissue is smooth muscle tissue and wherein the hollow shank portion of the needle is configured to penetrate smooth muscle tissue.

9. The arrangement of claim 7, wherein the tissue is uterine wall muscle tissue and wherein the hollow shank portion of the needle is configured to .penetrate the uterine wall muscle tissue.

10. The arrangement of claim 7, wherein there are a plurality of recording electrodes within the hollow shank portion spaced from one another.

11. The arrangement of claim 10, wherein there are a plurality of piezoelectric electrodes disposed within the hollow shank portion in alternating fashion among the recording electrodes.

12. A needle useful for monitoring gap junction discharges in a mass of tissue, the needle comprising:
  a shank with a point for penetrating the tissue and a bore extending from the point, wherein the bore receives a portion of the tissue therein to isolate the portion from the remaining mass of tissue;
  at least one recording electrode in the bore with a first lead extending therefore;
  at least one stimulating electrode in the bore with a second lead extending therefrom whereby upon applying a current pulse to the first lead to stimulate a gap junction discharge in the portion of tissue, the discharge is detected by the recording electrode for monitoring by a recording device connected to the first lead.

13. The needle of claim 12, wherein there are a plurality of recording electrodes each with a first lead.

14. The needle of claim 13, wherein there are a plurality of stimulation electrodes each with a second lead.

15. The needle of claim 13, further including an array of piezoelectric electrodes disposed among the recording electrodes.

* * * * *